United States Patent
Bluechel et al.

(10) Patent No.: US 8,961,574 B2
(45) Date of Patent: Feb. 24, 2015

(54) BONE PLATE WITH HOOK PORTION

(75) Inventors: Tobias Bluechel, Selzach (CH); Philip Henry, Biel/Bienne (CH); Denis Digeser, Freiburg (DE)

(73) Assignee: Stryker Trauma SA (CH)

( * ) Notice: Subject to any disclaimer, the term of this patent is extended or adjusted under 35 U.S.C. 154(b) by 0 days.

(21) Appl. No.: 13/596,576

(22) Filed: Aug. 28, 2012

(65) Prior Publication Data

US 2013/0053899 A1    Feb. 28, 2013

(30) Foreign Application Priority Data

Aug. 31, 2011    (EP) ...................................... 11007074

(51) Int. Cl.
*A61B 17/80* (2006.01)
*A61B 17/88* (2006.01)

(52) U.S. Cl.
CPC ......... *A61B 17/8061* (2013.01); *A61B 17/8014* (2013.01); *A61B 17/809* (2013.01)
USPC .............................. 606/297; 606/71; 606/281

(58) Field of Classification Search
CPC .............................. A61B 17/809; A61B 17/808
USPC ................................. 606/70–71, 280–299, 75
See application file for complete search history.

(56) References Cited

U.S. PATENT DOCUMENTS

| | | | | |
|---|---|---|---|---|
| 3,716,050 | A * | 2/1973 | Johnston | 606/286 |
| 5,006,120 | A * | 4/1991 | Carter | 606/71 |
| 5,931,839 | A * | 8/1999 | Medoff | 606/286 |
| 6,066,141 | A * | 5/2000 | Dall et al. | 606/74 |
| 7,229,444 | B2 * | 6/2007 | Boyd | 606/300 |
| 2004/0225291 | A1 | 11/2004 | Schwammberger et al. | |
| 2006/0235401 | A1 * | 10/2006 | Baldwin et al. | 606/69 |
| 2009/0012569 | A1 * | 1/2009 | Dall et al. | 606/280 |
| 2009/0275991 | A1 * | 11/2009 | Medoff | 606/297 |
| 2009/0312758 | A1 * | 12/2009 | Petit et al. | 606/60 |
| 2010/0137866 | A1 | 6/2010 | Gelfand | |
| 2010/0234896 | A1 * | 9/2010 | Lorenz et al. | 606/286 |
| 2011/0029025 | A1 * | 2/2011 | Medoff | 606/329 |
| 2011/0152943 | A1 * | 6/2011 | Gonzalez-Hernandez | 606/286 |

FOREIGN PATENT DOCUMENTS

| | | |
|---|---|---|
| JP | 2003210478 A | 7/2003 |
| WO | WO 2005074580 A2 * | 8/2005 |
| WO | 2010061410 A1 | 6/2010 |

OTHER PUBLICATIONS

Office Action for Application No. 11007074.5 dated Jun. 7, 2013.
Extended European Search Report for EP 11007074.5 dated Jan. 25, 2012.

* cited by examiner

*Primary Examiner* — Michael T Schaper
*Assistant Examiner* — Amy Sipp
(74) *Attorney, Agent, or Firm* — Lerner, David, Littenberg, Krumholz & Mentlik, LLP

(57) ABSTRACT

A bone plate for fixing bone fragments to bone is provided. The bone plate comprises an elongated body portion as well as a hook portion. The elongated body portion comprises an attachment opening configured to receive an attachment element for attaching the bone plate to bone. The hook portion extends from an end of the body portion and comprises one or more hooks configured to grasp a bone fragment. Additionally, at least one guiding opening is provided in the hook portion to receive an elongated guiding member for guiding the bone plate towards the bone fragment.

13 Claims, 3 Drawing Sheets

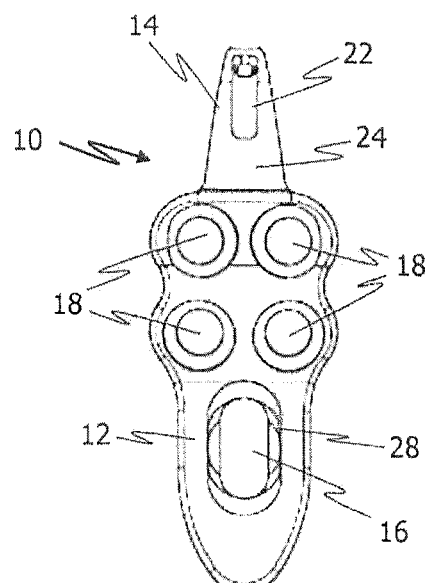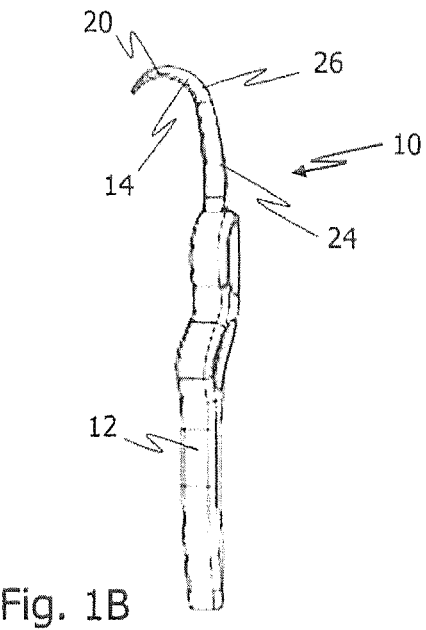
Fig. 1A         Fig. 1B
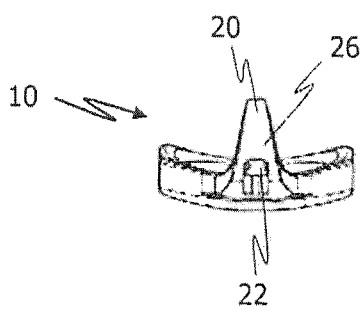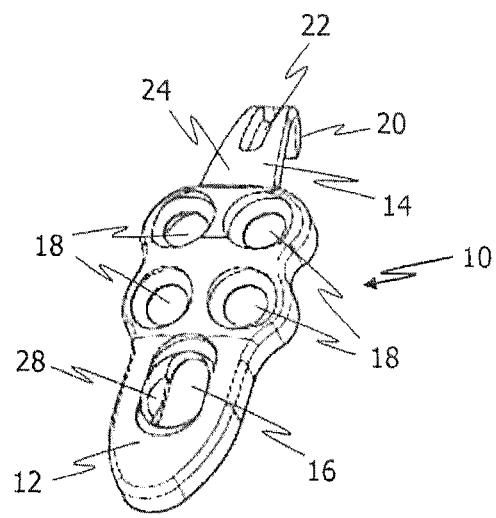
Fig. 1C         Fig. 1D

BONE PLATE WITH HOOK PORTION

FIELD OF THE INVENTION

The present disclosure generally relates to bone plates. In particular, a bone plate comprising a hook portion, also referred to as hook plate, is described.

BACKGROUND OF THE INVENTION

In certain surgical scenarios a small terminal bone fragment has to be fixed to a bone. Such scenarios comprise, for example, the treatment of fractures of the lateral malleolus. For many years, so-called hook plates have been used in such cases for fracture fixation.

U.S. Pat. Pub. No. 2009/0275991 A1 ("the '991 Application") describes a hook plate with an elongated body portion and a hook portion extending from one end of the body portion. The hook portion comprises two hooks for grasping a bone fragment. In the body portion, multiple attachment openings are provided for attaching the hook plate to the bone. The attachment openings include several circular screw holes as well as a further screw hole having an oblong form.

The '991 Application also describes a surgical procedure for fracture fixation using the hook plate. In an initial surgical step, pilot holes for the two hooks of the hook plate are drilled in a bone fragment. Then, the hooks are advanced into the pilot holes using a hammer. Full axial insertion of the hooks causes the elongate body portion to come to rest against the bone. In a final step, bone screws are inserted through the circular and oblong screw holes for a firm attachment of the hook plate at the bone.

There is a need for a hook plate that facilitates a surgical procedure of fixing a bone fragment to bone.

SUMMARY OF THE INVENTION

A bone plate for fixing bone fragments to bone is provided, wherein the bone plate comprises an elongate body portion having a longitudinal axis and comprising a first attachment opening configured to receive an attachment element for attaching the bone plate at least temporarily to bone, and a hook portion extending from an end of the body portion, wherein the hook portion comprises one or more hooks configured to grasp a bone fragment and at least one guiding opening configured to receive an elongated guiding member for guiding the bone plate towards the bone fragment.

The guiding opening may be substantially or fully closed. In such a realization, the elongated guiding member may be prevented from laterally exiting the guiding opening.

According to a first variant, the guiding opening has an essentially circular shape. In another variant, the guiding opening is realized as a slot. The slot may extend substantially parallel to the longitudinal axis of the elongated body portion.

In one realization, the guiding opening is configured to receive a wire as the guiding member. In such a realization, the dimensioning of the guiding opening (e.g., in terms of its diameter or width) may be slightly larger than a diameter of the wire. The guiding opening may additionally, or alternatively, be configured to receive a bone screw or a drill as the guiding member.

An end of the guiding member may be located at a bone fragment prior to sliding the hook plate along the guiding member to guide the hook plate towards the bone fragment. In one embodiment, a pre-drilled pilot hole is formed in the bone fragment in order to receive an end of the guiding member within the pilot hole.

One or more guiding openings may be located in various positions of the hook portion. As an example, one guiding opening may be located in the hook portion such that access to the bone fragment can be provided via the guiding opening (e.g., prior to attaching the bone plate to bone or in an implanted state of the bone plate). The hook portion of the bone plate may comprise an essentially straight part adjacent to the body portion and a bent part defining the one or more hooks. The guiding opening may be located in one or both of the essentially straight part and the bent part. When the guiding opening is realized as a slot, the guiding opening may substantially be located in the essentially straight part and, as an option, additionally extend into the bent part.

In certain cases, the guiding opening may be dimensioned smaller than the at least one first attachment opening. In this regard, the guiding opening may have a first dimension and the at least one first attachment opening (or any further attachment opening) may have a second dimension that is larger than the first dimension. In the case of a circular guiding opening or a circular attachment opening, the dimension may be defined by a diameter. In the case of a slot-like guiding opening or an oblong attachment opening, the dimension may be defined by a width of the opening.

The first attachment opening may have a circular or, alternatively, an oblong form. In case multiple first attachment openings are provided, one or more of the first attachment openings may be of a circular form and one or more other first attachment openings may have an oblong form.

The at least one first attachment opening may be configured as a compression hole for fracture reduction. In one implementation, the compression hole has an oblong form and is provided with a suitable structure at its periphery that permits creation of axial compression forces when an attachment member is attached to bone via the compression hole.

The body portion may comprise at least one second attachment opening configured to receive an attachment member for attaching the bone plate to bone. The at least one second attachment opening may be realized as a threaded or non-threaded circular hole. Two or more second attachment openings may be provided with centers that are located on an axis extending perpendicularly to the longitudinal axis of the body portion.

The body portion may have a first (e.g., maximum) width and the hook portion may have a second (e.g., maximum) width that is smaller or less than the first width. As an example, the body portion may have a maximum width which is between 9 mm and 13 mm, preferably 11 mm, and the hook portion may have a maximum width which is between 3 mm and 7 mm, preferably 5 mm.

Also provided is a bone plate system for fixing a bone fragment to bone. The bone plate system comprises the bone plate described herein and the elongated guiding member. The elongated guiding member may be configured as a wire or may have any other configuration (such as a drill configuration).

Also provided is a method of fixing bone fragments to bone. The method comprises locating an elongated guiding member at a bone fragment, inserting the guiding member into a guiding opening of a hook plate, sliding the hook plate along the guiding member to guide the hook plate towards the bone fragment, grasping the bone fragment by one or more hooks of the hook plate to bring the bone fragment close to the bone, and attaching the hook plate to the bone by inserting an attachment member through an attachment opening of the hook plate.

BRIEF DESCRIPTION OF THE DRAWINGS

Further details, advantages and aspects of the present disclosure will become apparent from the following embodiments taken in conjunction with the drawings, wherein:

FIG. 1A shows a top view of a first hook plate embodiment;

FIG. 1B shows a side view of the first hook plate embodiment;

FIG. 1C shows a front view of the first hook plate embodiment;

FIG. 1D shows a perspective view of the first hook plate embodiment;

DETAILED DESCRIPTION

Figure 2A:
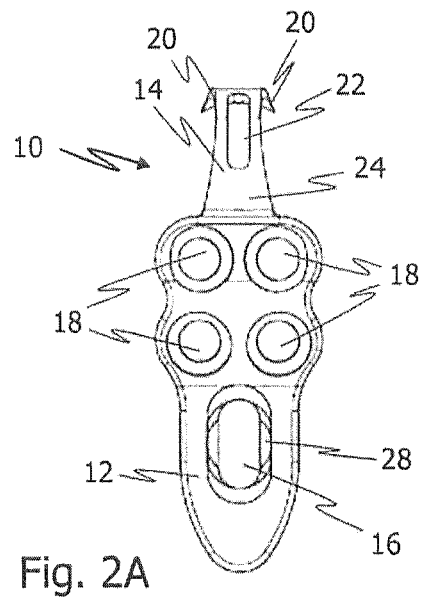
FIG. 2A shows a top view of a second hook plate embodiment.
Figure 2B:
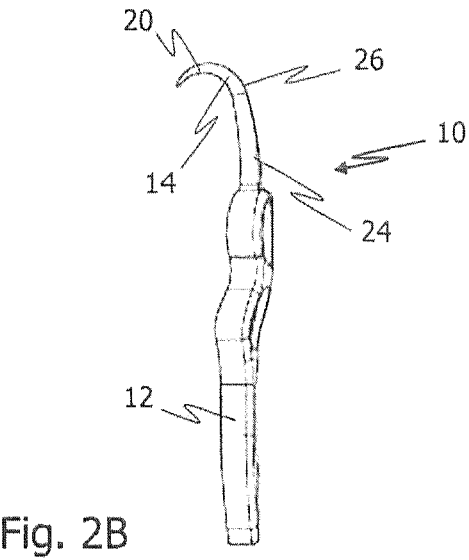
FIG. 2B shows a side view of the second hook plate embodiment.
Figure 2C:
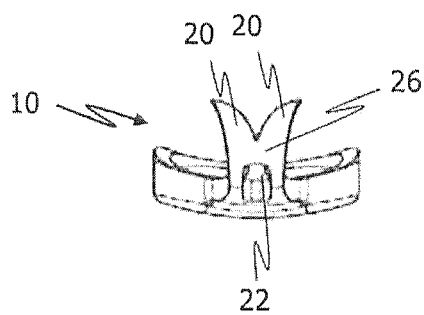
FIG. 2C shows a front view of the second hook plate embodiment.
Figure 2D:
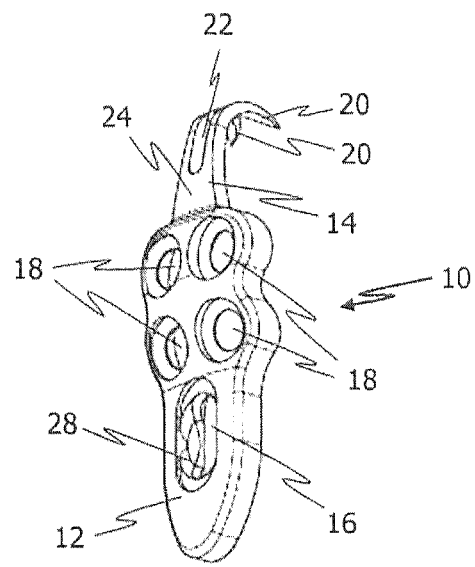
FIG. 2D shows a perspective view of the second hook plate embodiment.

In the following, several hook plate embodiments will be described. The same reference numerals will be used to denote the same or similar structural features of the hook plates.

FIGS. 1A-1D illustrate a first embodiment of a hook plate 10. The hook plate 10 is made from a bio-compatible material such as titanium and has an overall length which is between 20 and 40 mm. In the present embodiment, the overall length of the hook plate 10 is approximately 30 mm.

As illustrated in FIG. 1A, the hook plate 10 comprises an elongated body portion 12 and a hook portion 14 extending from an end of the body portion 12. The length of the body portion 12 amounts to 25±5 mm and the length of the hook portion is approximately 8 mm. In the body portion 12 multiple attachment openings 16, 18 are provided. The attachment openings 16, 18 are configured to each receive an attachment element (such as a bone screw, bone pin or bone peg) for attaching the bone plate 10 at least temporarily to a bone.

In the embodiment of FIGS. 1A-1D, the hook portion 14 comprises a single hook 20 configured to grasp a bone fragment that is to be fixed to bone. The hook portion 14 further comprises a guiding opening 22. The guiding opening 22 is closed and realized as a slot that extends substantially parallel to a longitudinal axis of the body portion 12.

The guiding opening 22 is configured to receive an elongated guiding member (such as a wire or drill) for guiding the bone plate towards the bone fragment. In the present embodiment, the guiding opening 22 has a length of approximately 5 mm and a width of approximately 1.5 mm. The width of the guiding opening 22 is selected to be slightly larger than the maximum dimension (e.g., the diameter) of the guiding member. As will be discussed below with reference to FIGS. 3A-3C, the guiding opening 22 is located in the hook portion 14 such that access to the bone fragment is obtained via the guiding opening 22. This access to the bone fragment facilitates guiding the bone plate 10 to the bone fragment along a longitudinal axis A-A.

As becomes apparent from the side view of FIG. 1B, the hook portion 14 comprises an essentially straight part 24 adjacent to the body portion 12 as well as a bent part 26 defining the hook 20. With reference to FIG. 1A, the guiding opening 22 is substantially located in the essentially straight part 24 and slightly extends into the bent part 26.

The body portion 12 has a maximum width of approximately 12 mm, and the hook portion 14 (at the end of the essentially straight part 24 adjacent to the body portion 12) has a maximum width which is between 3 mm and 7 mm and is in the present embodiment approximately 5 mm. The maximum width of the body portion 12 is thus larger than the maximum width of the hook portion 14. Moreover, as shown in the side view of FIG. 1B, the body portion has a larger maximum height (of approximately 2 mm) than the hook portion 14 (of approximately 1.2 mm).

With reference to FIGS. 1A and 1D, the attachment opening 16 is realized as an oblong compression hole for axial fracture reduction. To this end, the periphery of the attachment opening 16 is realized as a multi-facetted surface 28 that is intended to co-operate with a head of an attachment member. The surface 28 thus permits to exert compression forces in a direction parallel to the longitudinal axis of the body portion 12 upon insertion of the attachment member through the attachment opening 16 into the bone. The attachment opening 16 is provided at an end of the body portion 12 opposite the hook portion 14 and has a width which is between 3 mm and 13 mm and a length which is between 7 mm and 17 mm. In the present embodiment, the width of the attachment opening 16 is approximately 8 mm and the length of the attachment opening 16 is approximately 12 mm.

As also shown in FIGS. 1A and 1D, four further attachment openings 18 of circular shape are provided in a region between the attachment opening 16 and the hook portion 14. The diameter of each attachment opening 18 is approximately 3 mm. The centers of the four attachment openings 18 are approximately located on a square such that two pairs of attachment openings 18 are defined with the centres of each pair of attachment openings 18 being located on an axis extending perpendicularly to the longitudinal axis of the body portion 12.

While the hook plate 10 of the embodiment illustrated in FIGS. 1A-1D comprises a single hook 20 that extends along the longitudinal axis of the elongated body portion 12, other hook plate embodiments may comprise two or more hooks.

FIGS. 2A-2D illustrate an embodiment of a hook plate comprising two hooks 20. The two hooks 20 are provided on opposite sides of the longitudinal axis of the body portion 12 and extend laterally away from the longitudinal axis. The two hook realization illustrated in FIGS. 2A-2D prevents a rotation of the bone fragment grasp by the hooks 20. The remaining features of the hook plate 10 illustrated in FIGS. 2A-2D are identical to the corresponding features of the hook plate 10 illustrated in FIGS. 1A-1D and will thus not be described in more detail.

In the following, an embodiment of a surgical procedure for fixing a bone fragment to a bone using the hook plate 10 of FIGS. 1A-1D will be described with reference to FIGS. 3A-3D. The embodiment will be described for the exemplary case of treating an ulna fracture where a terminal bone fragment has to be re-attached to the ulna styloid.

Figures 3A, 3B, 3C, 3D:
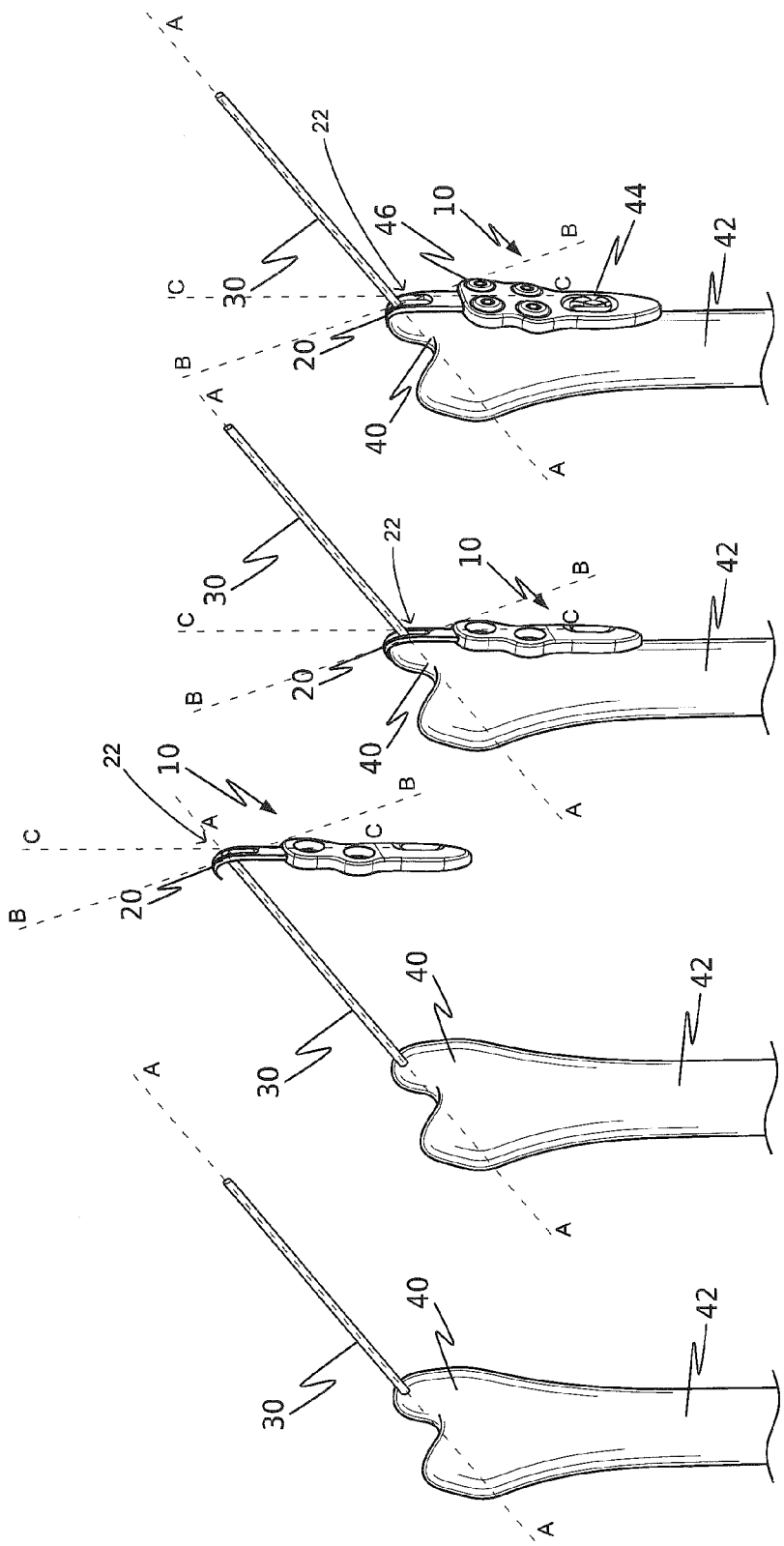
FIGS. 3A-3D illustrate a surgical procedure for fracture fixation using the hook plate illustrated in FIGS. 1A-1D.

In a first surgical step illustrated in FIG. 3A, a K-wire 30 is located at the bone fragment 40. To this end, a pilot hole is drilled into the bone fragment 40 and the K-wire 30 is introduced (e.g., screwed) into the pilot hole. Then, the bone fragment 40 is guided to the ulna 42 along the longitudinal axis A-A using the K-wire 30 as joystick.

As shown in FIG. 3B, the bone fragment 40 comes into abutment with the ulna 42, and the K-wire may, in one embodiment, be securely placed (e.g., screwed) in the ulna styloid. At this stage of the surgical procedure, the K-wire 30 is inserted into the guiding opening 22 of the hook plate 10 and the hook plate 10 is slided along the K-wire 30 towards the bone fragment 40 along longitudinal axis A-A. In this context, the K-wire 30 acts as an elongated guiding member for the hook plate 10 towards the bone fragment 42. FIG. 3C illustrates the location of the hook plate 10 when same has been brought to the ulna 42 over the K-wire 30 until the hook 20 starts to grasp the bone fragment 40 along a longitudinal axis B-B.

In a next step illustrated in FIG. 3D, fracture reduction is performed by axially pulling the hook plate 10 down along a longitudinal axis of the ulna 42 that is substantially parallel to a longitudinal axis C-C. To this end, a bone screw 44 in the form of a compression screw is inserted into the oblong attachment opening 16 that acts as compression hole. Upon inserting the bone screw 44, the bone fragment 40 is grasped tighter by the hook 20 of the bone plate 20 and pulled to the ulna 42 due to the co-operation of a head of the bone screw 44 with the multi-facetted surface 28 surrounding the attachment opening 16.

Once the desired fracture reduction has been achieved using the bone screw 44 for primary fixation, four additional bone screws 46 are introduced through the four attachment openings 18 for securing the bone plate 10 to the ulna 42. The bone screws 46 are realized as compression screws for achieving compression forces perpendicularly to the longitudinal axis of the ulna 42. If desired, the bone screw 44 may be removed again.

In a final step, the K-wire 30 is removed. After removal of the K-wire 30, a small bone screw may be introduced though the guiding opening 22 into the pilot hole of the bone fragment 20 for obtaining an additional fixation of the bone fragment 42 at the ulna 42.

As has become apparent from the surgical procedure described with reference to FIGS. 3A to 3D, the provision of the guiding opening 22 facilitates the placement of the hook plate 10 along longitudinal axis A-A. It will be appreciated that the form, size and position of the guiding opening 22 may be varied as needed.

While the present disclosure has been described with reference to exemplary embodiments, it will be appreciated that the present invention is not limited to what has been described above. Accordingly, it is intended that the present invention be limited only by the scope of the claims appended hereto.

The invention claimed is:

1. A system for fixing bone fragments to bone, the system comprising:
   an elongated guiding member having a longitudinal axis extending towards a bone fragment; and
   a bone plate having:
      an elongated body portion having a longitudinal axis and at least one attachment opening configured to receive an attachment element for attaching the bone plate at least temporarily to a bone;
      a hook portion extending from an end of the elongated body portion, the hook portion comprising one or more hooks configured to grasp a bone fragment; and
      at least one guiding opening in the hook portion, each guiding opening having:
         a longitudinal axis intersecting at least a portion of the longitudinal axis of the elongated body portion; and
         a continuous interior sidewall oriented at a non-parallel angle to the longitudinal axes of the elongated body portion and the guiding opening, the interior sidewall forming a guide hole shaped and sized to enable a sliding fit with the elongated guiding member,
   wherein the elongated guiding member precisely guides the bone plate towards the bone fragment, and
   wherein a portion of said guiding opening provides visual access to the bone fragment while the bone plate is guided along the elongated guiding member within said guiding opening.

2. The system of claim 1, wherein the at least one guiding opening forms a slot.

3. The system of claim 2, wherein the slot extends substantially parallel to the longitudinal axis of the elongated body portion.

4. The system of claim 1, wherein the hook portion comprises a substantially straight portion adjacent the elongated body portion and a curved portion defining the one or more hooks, wherein the at least one guiding opening is at least partially located in the substantially straight portion.

5. The system of claim 4, wherein the at least one guiding opening at least partially extends into the curved portion.

6. The system of claim 1, wherein the at least one guiding opening has a first dimension orthogonal to the longitudinal axis of the guiding opening and the at least one attachment opening has a second dimension orthogonal to the longitudinal axis of the elongated body portion of the bone plate that is larger than the first dimension.

7. The system of claim 1, wherein the at least one attachment opening has an oblong form.

8. The system of claim 7, wherein the at least one attachment opening is configured as a compression hole for fracture reduction.

9. The system of claim 1, wherein the at least one attachment opening comprises at least one first attachment opening configured to receive an attachment member for attaching the bone plate to bone and at least one second attachment opening configured as a compression hole for fracture reduction.

10. The system of claim 1, wherein the at least one attachment opening comprises at least two openings with centers that are located on an axis extending perpendicularly to the longitudinal axis of the elongated body portion.

11. The system of claim 1, wherein the elongated body portion has a first width along an axis orthogonal to the longitudinal axis of the bone plate and the hook portion has a second width along an axis orthogonal to the longitudinal axis of the bone plate that is less than the first width.

12. A system for fixing bone fragments to bone, the system comprising:
   an elongated guiding member having a longitudinal axis extending through a proximal and a distal end thereof, the distal end being proximate to a bone fragment; and
   a bone plate having:
      an elongated body portion having a longitudinal axis and at least one attachment opening configured to receive an attachment element for attaching the bone plate at least temporarily to a bone;
      a hook portion extending from an end of the elongated body portion, the hook portion comprising one or more hooks configured to grasp the bone fragment; and
      a guiding opening in the hook portion, the guiding opening having an continuous interior sidewall forming a guide hole and a longitudinal axis intersecting at least a portion of the longitudinal axis of the elongated body portion,
   wherein the guide hole is shaped and sized to enable a sliding fit with the elongated guiding member, wherein sliding the bone plate along the elongated guiding member within said guiding opening precisely guides the bone plate towards the bone fragment along the longitudinal axis of the elongated guiding member at a non-parallel angle to the longitudinal axes of the elongated body portion, and wherein a portion of said guiding opening provides visual access to the bone fragment while the bone plate is guided along the elongated guiding member within said guiding opening.

13. The system of claim 12, wherein the guiding opening of the bone plate is configured to receive a wire as the elongated guiding member.

\* \* \* \* \*